(12) United States Patent
Miller et al.

(10) Patent No.: US 11,358,912 B2
(45) Date of Patent: Jun. 14, 2022

(54) INCREASED OLIGOMER SELECTIVITY FROM OLEFIN OLIGOMERIZATION BY INCORPORATION OF BORON

(71) Applicant: PURDUE RESEARCH FOUNDATION, West Lafayette, IN (US)

(72) Inventors: Jeffrey T. Miller, West Lafayette, IN (US); Rajamani Gounder, West Lafayette, IN (US); Fabio H. Ribeiro, West Lafayette, IN (US); Han-Ting Tseng, West Lafayette, IN (US); Philip M. Kester, Lafayette, IN (US); Young Gul Hur, West Lafayette, IN (US); Yoon Rae Cho, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 102 days.

(21) Appl. No.: 16/635,664

(22) PCT Filed: Jul. 31, 2018

(86) PCT No.: PCT/US2018/044620
§ 371 (c)(1),
(2) Date: Jan. 31, 2020

(87) PCT Pub. No.: WO2019/028035
PCT Pub. Date: Feb. 7, 2019

(65) Prior Publication Data
US 2021/0122686 A1    Apr. 29, 2021

Related U.S. Application Data

(60) Provisional application No. 62/539,754, filed on Aug. 1, 2017.

(51) Int. Cl.
*C07C 2/12* (2006.01)
*C07C 11/02* (2006.01)

(52) U.S. Cl.
CPC .............. *C07C 2/12* (2013.01); *C07C 11/02* (2013.01); *C07C 2529/40* (2013.01); *C07C 2529/86* (2013.01)

(58) Field of Classification Search
CPC ....... C07C 2/12; C07C 11/02; C07C 2529/40; C07C 2529/86; C07C 5/2708; C07C 15/067; C07C 2/66; C07C 15/02
See application file for complete search history.

(56) References Cited

U.S. PATENT DOCUMENTS

| | | |
|---|---|---|
| 5,393,407 A | 2/1995 | Zones et al. |
| 6,342,200 B1 | 1/2002 | Rouleau et al. |
| 2015/0197463 A1 | 7/2015 | Corma Canos et al. |

OTHER PUBLICATIONS

International Search Report and Written Opinion for International Application No. PCT/US2018/044620 dated Feb. 5, 2019.

(Continued)

*Primary Examiner* — Sharon Pregler
(74) *Attorney, Agent, or Firm* — Edmonds & Cmaidalka, P.C.

(57) ABSTRACT

A novel catalyst composition and its use in the oligomerization reactions of light alkenes to higher molecular weight hydrocarbons. The catalyst comprises boron added to an Al-containing or Ga-containing or Fe-containing support. The catalyst composition is an active and selective catalyst for the catalytic oligomerization reactions of light alkenes to higher molecular weight hydrocarbons.

16 Claims, 7 Drawing Sheets

(56) References Cited

OTHER PUBLICATIONS

Andersen; "Propene Oligomerization Over Steam Dealuminated and Boron and Phosphorous Modified ZSM-5"; University of Cape Town; Jun. 1991; <https://open.uct.ac.za/handle/11427/22049>; p. 36, para 1-2; p. 37, para 2; p. 46, para 2; p. 64, para 2; p. 89, para 1, 3; p. 91, para 1; p. 93, para 2; p. 95, para 2; p. 99, para 1; p. 100, para 1-2, Table 3.12; p. 129, para 1; p. 141, para 3.

Tong; "Boron Coordination and Co-incorporation of Al, Ga in *BEA Borosilicate and Dissolution of Zeolite Nanoparticles from Large Particles in Organic Solvents"; Westfalischen Wilhelms-Universitat Munster; 2007; <https://www.youscribe.com/catalogue/documents/savoirs/boron-coordination-and-co-incorporation-of-al-ga-in-bea-1425540>; p. 9, para 1.

SEM Images of B-Al-MFI Synthesized at Purdue

|←2 μm→|

B-Al-MFI-0.23

|←2 μm→|

B-Al-MFI-0.46

|←10 μm→|

B-Al-MFI-0.28

|←20 μm→|

B-Al-MFI-0.56

INCREASED OLIGOMER SELECTIVITY FROM OLEFIN OLIGOMERIZATION BY INCORPORATION OF BORON

BACKGROUND

The present disclosure is directed to new catalyst compositions for the oligomerization of light alkenes, especially gaseous alkenes, e.g., ethene, propene, butenes and pentenes, to their respective higher molecular weight hydrocarbon derivatives. The longer chain higher molecular weight hydrocarbons have a greater value than the lighter alkenes.

More efficient utilization of petroleum and gas reserves is an important strategy for the deployment of future energy generation. Shale gas has become an increasingly important source of natural gas in the United States, and the U.S. government's Energy Information Administration predicts that by 2040, approximately 70 percent of the United States' natural gas supply will come from shale gas. The transformation of shale gas to transportation fuels, fine chemicals and additives is one of the strategies to utilize the shale gas reserves to their highest value.

Light alkene oligomerization is a promising pathway to synthesize higher molecular weight hydrocarbons for transportation fuels and additives. Solid acids including supported phosphoric acid, acid resins, amorphous silica-alumina, and zeolites have been used in industrial oligomerization processes, with MFI framework zeolites garnering the most attention for these reactions due to its resistance to coke formation and high selectivity to linear olefins with high cetane number. MFI zeolites in their aluminosilicate composition are also known as ZSM-5. ZSM-5 is used in the Mobil Olefins to Gasoline and Distillate (MOGD) process, and there are several patents from the 1980s associated with this process.

Zeolites contain tetrahedral silicon atoms linked by oxygen, forming charge-neutral crystalline structures. The isomorphous substitution of trivalent aluminum atoms into the crystalline structure for tetravalent silicon introduces a negative charge imbalance that can be compensated by protons, which act as Brønsted acid sites for catalysis. Zeolites, molecular sieves, and related microporous and mesoporous materials have the ability to control the access of reactants and products, based on their size and shape, to catalytically active sites within the pores of these materials. Thus, they can preferentially contain only those transition states that can be stabilized while excluding others. These phenomena have been described as concepts of shape selectivity and size exclusion and are considered to be a hallmark of zeolite catalysis.

Oligomerization can also be accompanied by an undesired cracking (β-scission) reaction to form smaller hydrocarbons from oligomers. High selectivity is strived for by preferentially slowing cracking reactions relative to oligomerization. However, the selectivity of this reaction is insensitive to the strength of the solid acid since β-scission is the microscopic reverse reaction of oligomerization, thus stabilization of intermediates or transition states affects these pathways to the same extent. Other synthetic variables that may affect the product distribution of olefin oligomerization in zeolites include local aluminum proximity and the interplay between crystal size and bulk aluminum content.

There is a need for improved catalysts for use in alkene dimerization and oligomerization reactions that provide improved selectivity while also enabling acceptable conversion rates.

BRIEF DESCRIPTION OF THE DRAWINGS

The accompanying drawings are incorporated into and form a part of the specification to illustrate aspects and examples of the present disclosure. These figures together with the description serve to explain the general principles of the disclosure. The figures are only for the purpose of illustrating examples of how the various aspects of the disclosure can be made and used and are not to be construed as limiting the disclosure to only the illustrated and described examples.

DETAILED DESCRIPTION

Figure 1:
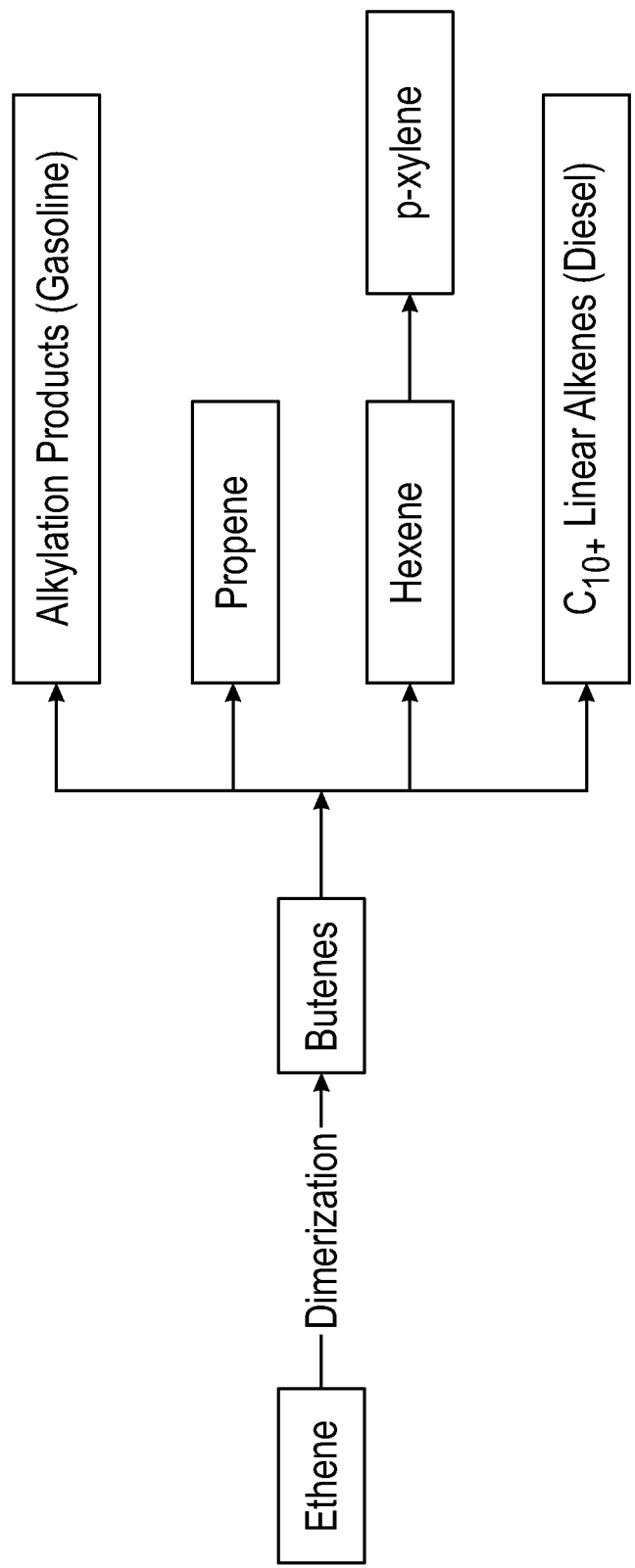
FIG. 1 is a block flow diagram of ethene oligomerization that forms an entry step chemistry to form higher molecular weight compounds.

The following detailed description illustrates embodiments of the present disclosure. These embodiments are described in sufficient detail to enable a person of ordinary skill in the art to practice these embodiments without undue experimentation. It should be understood, however, that the embodiments and examples described herein are given by way of illustration only, and not by way of limitation. Various substitutions, modifications, additions, and rearrangements may be made that remain potential applications of the disclosed techniques. Therefore, the description that follows is not to be taken as limiting on the scope of the appended claims. In particular, an element associated with a particular embodiment should not be limited to association with that particular embodiment but should be assumed to be capable of association with any embodiment discussed herein.

Definitions

For the purpose of this description and appended claims, the following terms are defined.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All processes described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The term "alkane" or "paraffin" means substantially saturated compounds containing hydrogen and carbon only, e.g., those containing ≤1% (molar basis) of unsaturated carbon atoms. The term alkane encompasses $C_1$ to $C_6$ linear, iso, and cyclo alkanes.

As used herein, an "alkene" or "olefin" refers to any unsaturated hydrocarbon containing one or more pairs of carbon atoms linked by a double bond. The olefins described herein include cyclic or aliphatic olefins, and include mono-olefins, di-olefins, tri-olefins, etc.

The term "$C_n$" hydrocarbon wherein n is a positive integer, e.g., 1, 2, 3, 4, or 5, means hydrocarbon having n carbon atom(s) per molecule. The term "$C_{n+}$" hydrocarbon wherein n is a positive integer, e.g., 1, 2, 3, 4, or 5, means hydrocarbon having at least n carbon atom(s) per molecule. The term "$C_{n-}$" hydrocarbon wherein n is a positive integer, e.g., 1, 2, 3, 4, or 5, means hydrocarbon having no more than n number of carbon atom(s) per molecule.

As used herein, a "catalyst" is any substance or material that changes the rate of conversion of alkenes to higher molecular weight hydrocarbons but is not, itself, consumed.

The term "hydrocarbon" means compounds containing hydrogen bound to carbon, and encompasses (i) saturated hydrocarbon, (ii) unsaturated hydrocarbon, and (iii) mixtures of hydrocarbons, including mixtures of hydrocarbons (saturated and/or unsaturated) having different values of n.

The term "zeolite" means microporous, crystalline silicon oxide minerals commonly used as commercial adsorbents and catalysts.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The present disclosure relates generally to oligomerization reactions of light alkenes to higher molecular weight hydrocarbons. More particularly, the present disclosure relates to catalysts that can enable oligomerization reactions of light alkenes to higher molecular weight hydrocarbons substantially free of aromatic hydrocarbons. Substantially free shall herein mean less than about 5 weight percent aromatic hydrocarbons. Embodiments of the present disclosure provide a method to produce such catalysts.

The present disclosure presents novel catalyst compositions and their respective use in the oligomerization reactions of light alkenes to higher molecular weight hydrocarbons. The catalyst contains trivalent boron substituted for tetravalent silicon atoms within a support matrix. The boron substituted for silicon is an effort to control the crystallite size and Brønsted acid site content in the support and to alter the selectivity toward various oligomer products. The catalyst is an active and selective catalyst for the catalytic oligomerization of light alkenes to higher molecular weight hydrocarbons while retaining high activity and selectivity even following repeated regeneration.

The oligomerization of light olefins (alkene molecules having from 2 to 6 carbon atoms) is an important industrial reaction and represents a route to the production of intermediates used for the production of motor fuels, plasticizers, pharmaceuticals, dyes, resins, detergents, lubricants and additives. The oligomerization of light olefins, such as ethene and propene, represents an important industrial route to the production of environmentally friendly synthetic liquid products, free of sulphur and aromatics. Thus, ethene oligomerization forms an entry step chemistry to form higher molecular weight compounds, which is shown in the block flow diagram of FIG. 1.

Zeolites contain tetrahedral silicon atoms linked by oxygen, forming charge-neutral crystalline structures. The isomorphous substitution of trivalent aluminum atoms for tetravalent silicon introduces a negative charge imbalance that can be compensated by protons, which act as Brønsted acid sites for catalysis. Here, we synthesize zeolites with boron and aluminum atoms for simultaneous control of crystal size and aluminum content and show that the selectivity toward oligomers of propene is enhanced using these materials, compared to commercially available zeolites synthesized by conventional methods that only contain aluminum heteroatoms with similar bulk aluminum contents and crystal sizes. The substitution of trivalent boron atoms for tetravalent silicon atoms also are compensated by protons, but of much weaker acid strength that do not behave as Brønsted acid sites for catalysis.

The present disclosure relates to efforts to control the crystallite size and Brønsted acid site content in zeolites and to alter the selectivity toward various oligomer products. It has been found that independent and simultaneous control of the crystallite size and Brønsted acid site content in MFI zeolites can be achieved with addition of boron to the zeolite synthesis mixture. It has further been found that selectivity toward oligomer products in propene oligomerization is enhanced in B—Al-MFI over conventional Al-MFI catalysts prepared with similar crystal sizes and bulk aluminum content.

The catalysts of the present disclosure can be prepared by making a precursor solution containing boron and aluminum. The precursor solution is contacted with a silicon source, such as colloidal silica, mixed and heated, and then solids recovered via centrifugation. The resulting solids are then dried, and occluded organic molecules removed via calcination.

The present disclosure is not limited by the method of catalyst preparation, and all suitable methods should be considered to fall within the scope herein. The synthesis mixture can be accomplished via any suitable techniques known to those skilled in the art. Conventional methods include co-precipitation from an aqueous, an organic, or a combination solution-dispersion, impregnation, dry mixing, wet mixing or the like, alone or in various combinations. In general, any method can be used which provides compositions of matter containing the prescribed components in effective amounts.

The boron and/or aluminum, or boron and/or gallium, or boron and/or iron can be added in any suitable manner known in the art, such as by addition of a solid, as a solution, precipitation, and gel formation. The boron and/or aluminum, or boron and/or gallium, or boron and/or iron, can be added to a zeolite. The boron and/or aluminum, or boron and/or gallium, or boron and/or iron, can be added to a MFI zeolite. The boron can be added to an aluminosilicate, gallosilicate or ferrosilicate zeolite. The boron can be added to a ZSM-5 zeolite.

Frequently, the pH of the solution will be adjusted to provide for optimum crystallization. In an embodiment the pH can be limited to between 8-14, optionally between 9-13, optionally between 10-12, optionally the pH can be held at a desired value throughout the crystallization procedure.

Crystallization time can be anywhere from at least about 1 minute to about 1 month, optionally about 1 hour to 1 week, optionally, about 1 to about 24 hours. In some instances, the higher the crystallization temperature the shorter the crystallization time that is necessary. Such crystallization times can be readily determinable by one skilled in the art. The resulting material can then be separated by any conventional means, washed and dried. The crystalline B—Al-MFI zeolite can then be dried followed by steps such as calcination and reduction.

The drying can be conducted at ambient temperature at first, such as for about 3 hours, followed by an elevated temperature, such as about 125° C. for about 4-10 hours. The calcination can be conducted at increasingly elevated temperature, such as at a temperature from 200° C. to 650° C., in the presence of oxygen, or in an air stream, or in the presence of a mixture of oxygen and an inert gas. In an example, the calcination can be about 200° C. for 30 minutes, and then 550° C. for 30 minutes or longer. The calcination process can be a staged calcination, wherein the temperatures are changed throughout the process. The temperature changes need not be a linear increase, but can be increased for example from 200° C. to 400° C. and held at 400° C. followed by another increase, etc. However, linear increases in temperature can also be used. This calcination can be conducted for periods ranging from about 30 minutes to 24 hours in either flowing or static gases. The times, temperatures and rates of change during the drying and calcination process of the crystalline B-A-MFI zeolite are variable, can be readily determinable by one skilled in the art, and is not to be a limitation upon the present disclosure.

The various elements that make up the components for the catalyst can be derived from any suitable source, such as in their elemental form, or in compounds or coordination complexes of an organic or inorganic nature, such as carbonates, oxides, hydroxides, nitrates, acetates and chlorides. The elements and/or compounds can be prepared by any suitable method known in the art for the preparation of such materials.

The supports of the present disclosure can be any suitable support, such as for non-limiting examples: silicon dioxide, aluminum oxide, titanium dioxide, silica pillared clays, metal modified silica, metal oxide modified silica, silica-pillared clays, metal oxide modified silica-pillared clays, silica-pillared micas, metal oxide modified silica-pillared micas, silica-pillared tetrasilicic mica, silica-pillared taeniolite, and combinations thereof. Such supports are commercially obtainable or prepared by techniques known to those skilled in the art.

When slurries, precipitates or the like are prepared, they will generally be dried, usually at a temperature sufficient to volatilize the water or other carrier, such as from 100° C. to 250° C., with or without vacuum. Irrespective of how the components are combined and irrespective of the source of the components, the dried composition can be calcined in the presence of a free oxygen-containing gas, usually at temperatures between about 300° C. and about 800° C. for from 1 to 24 hours. The calcination can be in an oxygen-containing atmosphere, or alternately in a reducing or inert atmosphere.

Binder material, extrusion aids or other additives can be added to the catalyst composition or the final catalyst composition can be added to a structured material that provides a support structure. For example, the catalyst component and/or the composite catalyst can include an alumina or aluminate framework as a support. Upon calcination these elements can be altered, such as through oxidation which would increase the relative content of oxygen within the final catalyst structure. The combination of the composite catalyst of the present invention combined with additional elements such as a binder, extrusion aid, structured material, or other additives, and their respective calcination products, are included within the scope of the invention.

The prepared catalyst can be ground, pressed, sieved, shaped and/or otherwise processed into a form suitable for loading into a reactor. The reactor can be any type known in the art, such as a fixed bed, fluidized bed, or swing bed reactor. Optionally an inert material, such as quartz wool, can be used to support the catalyst bed and to locate the catalyst within the bed. Depending on the catalyst, a pretreatment of the catalyst may, or may not, be necessary. For the pretreatment, the reactor can be heated to elevated temperatures, such as 200° C. to 800° C. with an air flow, such as 100 mL/min, and held at these conditions for a length of time, such as 1 to 3 hours. Then, the reactor can be brought to the operating temperature of the reactor, for example 150° C. to 500° C., or optionally down to atmospheric or other desired temperature. The reactor can be kept under an inert purge, such as under a nitrogen or helium purge.

The catalyst of the present disclosure can be contacted with a feedstream containing $C_2$ to $C_5$+ alkenes under oligomerization conditions, for a time and at a temperature sufficient to produce higher molecular weight hydrocarbons, substantially free of aromatic hydrocarbons. It is desirable that mono-olefins or linear paraffin hydrocarbons will be produced. The alkenes may be co-fed with a stream of $H_2$ and/or inert gas. The $H_2$:alkene or inert:alkene ratio can range from about 0 to 5, optionally 0 to 1.0. Steam may also be co-fed if desired as a diluent or as a heat transfer agent.

In an embodiment the catalyst of the present disclosure can undergo in-situ regeneration, which can lower operating costs by decreasing the amount of time the reactor must be offline. The regeneration can be done by hydrogen and water vapor stripping at the reaction temperature. In an embodiment the catalyst of the present disclosure can undergo ex-situ regeneration.

In another embodiment, the disclosure is a process for the oligomerization of light alkenes to produce higher molecular weight hydrocarbons. The process includes the steps of introducing an alkene feedstock into a reaction chamber, passing the feedstock over an oligomerization catalyst at reaction conditions effective to provide a product containing higher molecular weight hydrocarbons, and regenerating the catalyst in-situ, when necessary.

The alkene feedstock can be alkenes containing less than 10 carbon atoms, optionally less than 8 carbon atoms, optionally less than 6 carbon atoms. The feedstock can consist primarily of $C_2$-$C_6$ alkenes. An embodiment of the invention provides for the use of ethene or propene or butene or a mixture of these gases as the feedstock. The alkene feedstock can be obtained from the side product of various hydrocarbon processing plants, for instance, the offgas of an FCC cracker, steam cracker, or alkane dehydrogenation process.

One source of alkene feedstock is from ethane cracking plants, often the ethane separated from the NGL's that are extracted from a gas stream, such as a gas stream produced from a shale formation. Co-feed can contain hydrogen. In an illustrative embodiment the alkene feed can contain primarily ethene. In an illustrative embodiment the alkene feed can contain primarily propene. In an illustrative embodiment the alkene feed can contain primarily butene. In an illustrative embodiment the alkene feed can contain primarily ethene and propene. In an illustrative embodiment the alkene feed can contain primarily propene and butene. In an illustrative embodiment the alkene feed can contain primarily butene and pentene. In an illustrative embodiment the alkene feed can contain primarily $C_3$-$C_6$ alkenes. In an illustrative embodiment the alkene feed can contain primarily $C_4$-$C_6$ alkenes.

The reaction chamber can house any suitable catalyst system, such as a fixed catalyst bed, a moving bed or a fluidized bed. Single or multiple catalyst beds can be used, and the reactor can be a swing reactor. The catalysts described herein may be used in any suitable reactor. The process could utilize a series of fixed bed reactors, where each reactor could be independently regenerated, a moving bed reactor where the catalysts moves through the reactor and is regenerated in a separate section of the plant, or a fluidized bed reactor, where the catalyst is circulated through the reactor and regenerated in a separate vessel.

The reaction can take place at a temperature of from 100° C. to 500° C., optionally from 150° C. to 450° C. For example, the reaction may take place at up to 150° C., 200° C., 250° C., 300° C., 350° C., 400° C., 450° C., or 500° C. The pressure can be in the range of from 3 psig to 1500 psig, optionally from 15 psig to 1000 psig, optionally from 15 psig to 500 psig. The weight hourly space velocity can be from 0.3 to 20 $hr^{-1}$, optionally from 0.3 to 10 $hr^{-1}$, and optionally from 0.3 to 5 $hr^{-1}$.

The oligomerization reaction can be performed adiabatically or non-adiabatically or approximately isothermally. If the oligomerization is performed in an adiabatically operated catalyst bed, the exothermic reaction will cause the temperature to increase over the length of the catalyst bed. The reaction selectivity in the catalyst bed is thus limited so that several catalyst beds are typically required to achieve the desired high selectivity and cooling downstream of each catalyst bed. In order to achieve reasonable reaction rates, several catalyst beds are normally arranged in series and the reaction system is cooled downstream of each catalyst bed.

If the oligomerization is performed in a non-adiabatically operated catalyst bed, the catalyst bed can be heated in order to maintain a high temperature. Because of the fact that the temperature in the reaction system is kept constant, the reaction rates may be kept appropriately high. Because of the location of the point of thermodynamic equilibrium, however, the disadvantage is that these high reaction rates can only be achieved at high temperatures, as a result of which the selectivity of olefin formation may be reduced. Hence, consecutive reactions will increasingly take place, so that undesired products may form, such as $C_3H_8$, i-$C_4H_{10}$, higher branched alkanes, aromatics and coke.

The by-products thus formed, especially finely dispersed coke, can precipitate in the course of the reaction on the catalyst, thus causing its state to change continually. The catalyst becomes coated with an undesired substance and is thus less accessible for the reactants. This means that the catalyst becomes deactivated. The activity of the catalyst for alkene oligomerization and the selectivity for the desired product may in turn deteriorate. This would result in deterioration of the efficiency of the process as a whole. Because of operational requirements, such a deactivation can only be tolerated up to certain limit, because an economically viable operation of the plant could no longer be guaranteed. In order to counter-act this negative influence on the process, the catalyst will have to be regenerated after a certain reaction period in order to recover its activity.

Depending on its characteristics, the catalyst can be regenerated by bringing it in contact with an oxygen-bearing gas under conditions defined for the regeneration of the catalyst. The conditions for such regeneration may differ from those required for the oligomerization. An oxygen-bearing gas diluted with steam may also be fed through the catalyst. As a result of this procedure, the by-products on the catalyst are reduced, with the result that the catalyst can regain its activity. If an oxygen-bearing gas diluted with steam is used for catalyst regeneration, the carbon-bearing deposit reacts to form carbon dioxide as the main product. The carbon-bearing deposit is converted to gaseous products by this reaction and is removed from the system.

As the conditions for the alkene oligomerization process differ from the catalyst regeneration process, the alkene oligomerization process will be interrupted after a certain period of operation and substituted by the catalyst regeneration process. Thereafter, the reactor bed is purged and again made available for oligomerization. Both these processes, i.e. the alkene oligomerization and catalyst regeneration, are thus performed periodically. In order to render the overall process economically efficient, this can take place in two or a plurality of catalyst beds, in which the reaction and regeneration processes are alternately implemented. In order to ensure optimum catalyst regeneration, regeneration process should be instrumented and monitored.

The reaction products can be processed and separated by cooling or other standard recovery or separation techniques.

The following examples are given to provide a better understanding of the present invention and are not intended to limit the scope of the invention in any way.

EXPERIMENTAL DATA

A commercially available MFI catalyst was obtained from Zeolyst International with a nominal Si/Al ratio of 140 (CBV 28014, Lot #2200-86).

MFI catalysts containing boron and aluminum heteroatoms were made via hydrothermal synthesis protocols. Molar ratios of the synthesis solution were 1 $SiO_2$/X $A(NO_3)_3$/Y $H_3BO_4$/0.3 EDA/0.042 TPABr/15.1 $H_2O$, with X=0.006, 0.011 and Y=0.077, 0.39. In a typical synthesis, 1.503 g of ethylenediamine (EDA, 99.5 wt %, Sigma Aldrich) was first diluted in 6.023 g of deionized water (18.2 MΩ) in a perfluoroalkoxy alkane (PFA) jar. Next, 0.392 or 1.997 g (for Si/B=2.6 or 13) of boric acid ($H_3BO_4$, 99.5 wt %, Sigma Aldrich) was added to the mixture and allowed to stir under ambient conditions for 15 minutes. In a separate PFA jar, 0.183 or 0.353 g (for Si/Al=176 or 88) of aluminum nitrate nonahydrate ($Al(NO_3)_3 \cdot 9\ H_2O$, 98 wt %, Sigma Aldrich) was diluted in 9.383 g of deionized water, followed by the addition of 0.286 g of tetra-n-propylammonium bromide (TPABr, 98 wt %, Alfa Aesar). This mixture was also stirred for 15 minutes under ambient conditions. The two mixtures were then combined, and 12.513 g of colloidal silica (Ludox HS40, 40 wt %, Sigma Aldrich) was added to the mixture and stirred for 2 hours under ambient conditions. The synthesis solution was then transferred to a 45 ml Teflon-lined stainless steel autoclave (Parr Instruments) and placed in a forced convection oven (Yamato DKN-402C) at 443 K and rotated at 40 rpm for 5 days. Solids were recovered, washed with deionized water (150 cm³ per g solids), recovered via centrifugation, and dried at 373 K under stagnant air for 24 hours. Occluded organic molecules were removed via calcination in flowing dry air (1.67 cm³ s$^{-1}$ $g_{cat}^{-1}$, 99.999% UHP, Indiana Oxygen) at 853 K (0.0167 K s$^{-1}$) for 10 hours.

All MFI catalysts were converted into their $NH_4$-form by ion-exchange in aqueous 1M $NH_4NO_3$ solution (98%, Sigma Aldrich) for 24 hours under ambient conditions, followed by calcination in flowing dry air (1.67 cm³ s$^{-1}$ $g_{cat}^{-1}$, 99.999% UHP, Indiana Oxygen) at 773 K (0.0167 K s$^{-1}$) for 4 hours to convert to their H-form.

The crystalline structure of synthesized materials was determined from powder X-ray diffraction (XRD) patterns measured on a Rigaku SmartLab X-ray diffractometer with a Cu Kα source (λ=0.154 nm) operated at 1.76 kW. Diffraction patterns were measured from 4-40° 2θ. All patterns collected were consistent with the MFI topology. Zeolite micropore volumes were calculated from Ar adsorption isotherms collected at 87 K for H-MFI samples in a Micromeritics ASAP 2020 Surface Area and Porosity Analyzer by extrapolating the linear volumetric uptake at the beginning of mesopore filling (~0.05-0.30 P/$P_0$). All micropore volumes were typical of highly crystalline MFI structure (0.12-0.15 cm³ g$^{-1}$).

Bulk aluminum contents of the commercially available and synthesized MFI zeolites were determined via atomic absorption spectroscopy (AAS) using a PerkinElmer AAnalyst 300 Atomic Absorption Spectrometer. Samples were prepared by dissolving 0.2 g of zeolite in 2 g of hydrofluoric acid (48 wt %, Sigma Aldrich), allowing the solution to sit overnight, followed by addition of 50 g of deionized water (18.2 MΩ). Absorbances were measured with a radiation source of 309.3 nm in a reducing acetylene/nitrous oxide flame and compared to calibration curves produced from known solutions.

Crystal sizes of B—Al-MFI were estimated with scanning electron microscopy (SEM) on an FEI Quanta 3D FEG Dual-beam SEM. Prior to imaging, samples were coated with platinum to reduce charging of the insulating materials. Images were collected with an accelerating voltage of 15 kV and spot size of 6 at 10,000×-35,000× magnification.

Figure 2:
FIG. 2 shows SEM images of B-A-MFI catalyst synthesized at Purdue.
Figure 2:
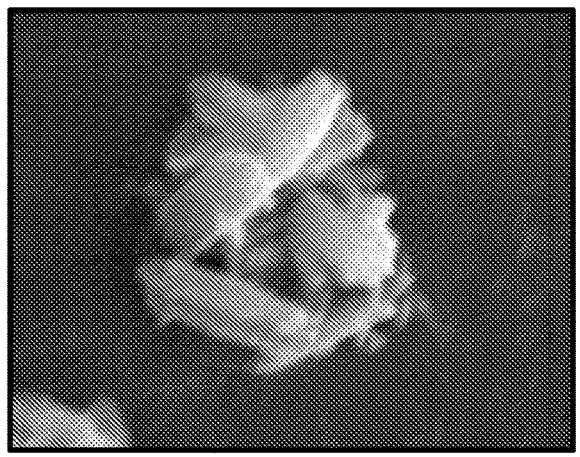
Figure 2:
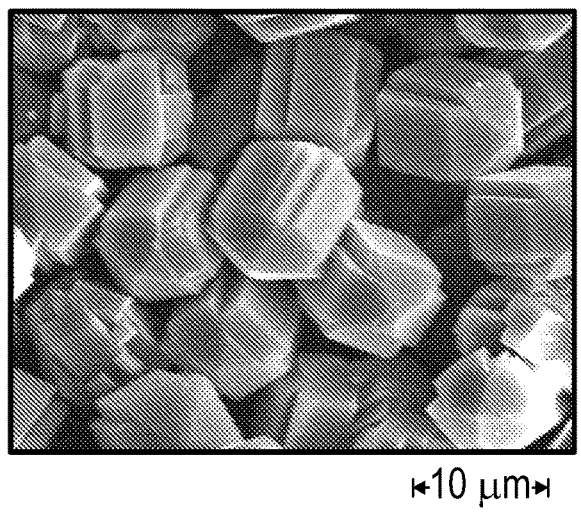
Figure 2:
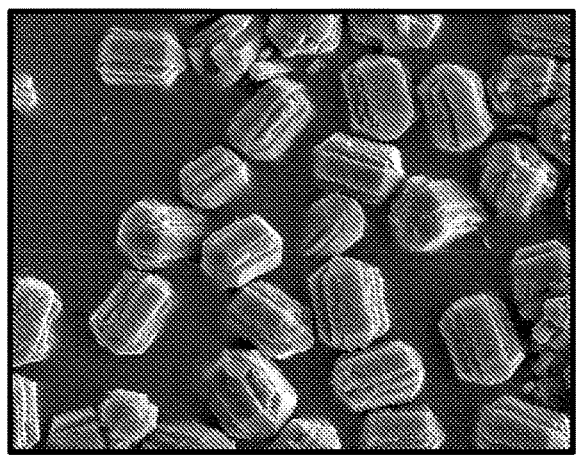
Figure 3:
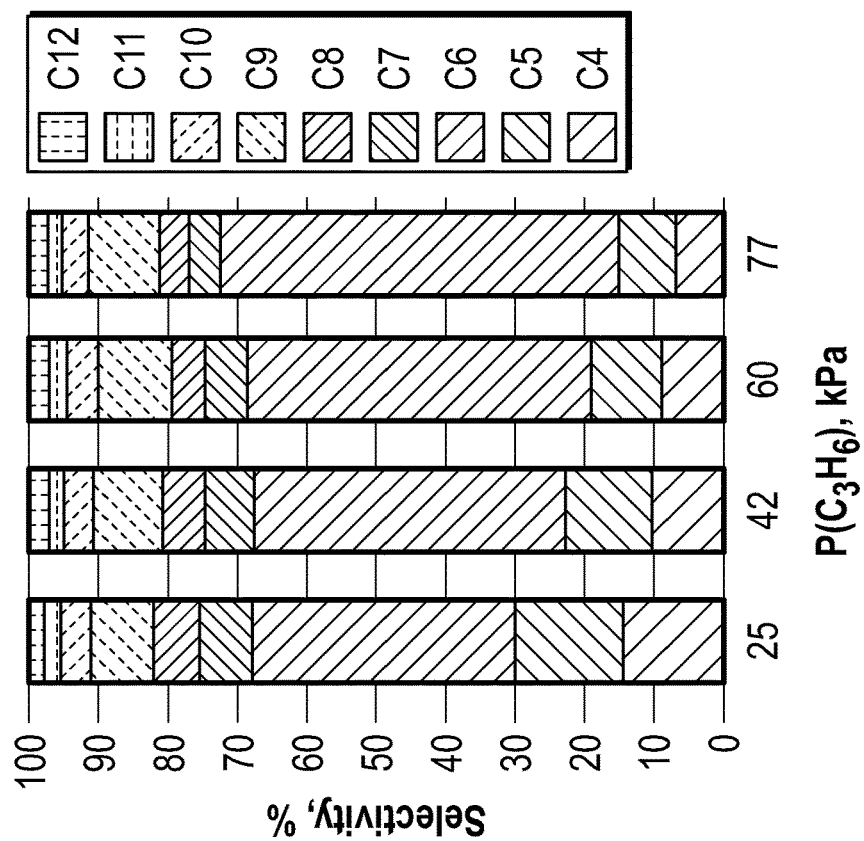
FIG. 3 is a bar graph of product distribution of propene oligomerization on commercial Al-MFI-0.32 catalyst at 251° C., 1 atm total pressure with propene partial pressures of 25 to 77 kPa.
Figure 4:
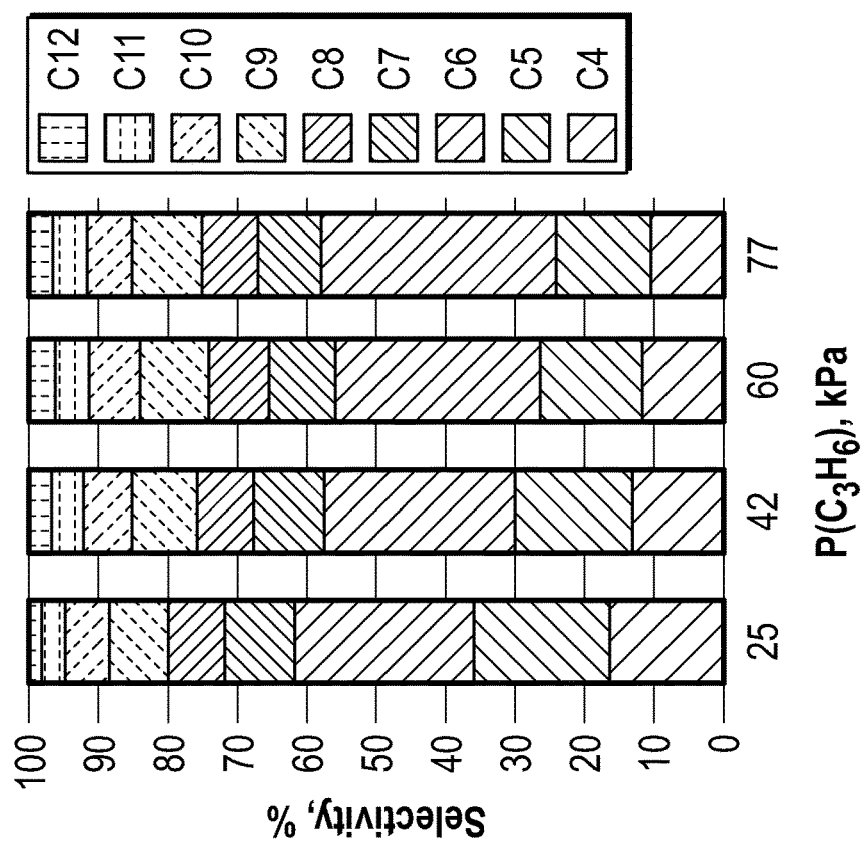
FIG. 4 is a bar graph of product distribution of propene oligomerization on a B-A-MFI-0.56 catalyst at 251° C., 1 atm total pressure with propene partial pressures of 25 to 77 kPa.
Figure 5:
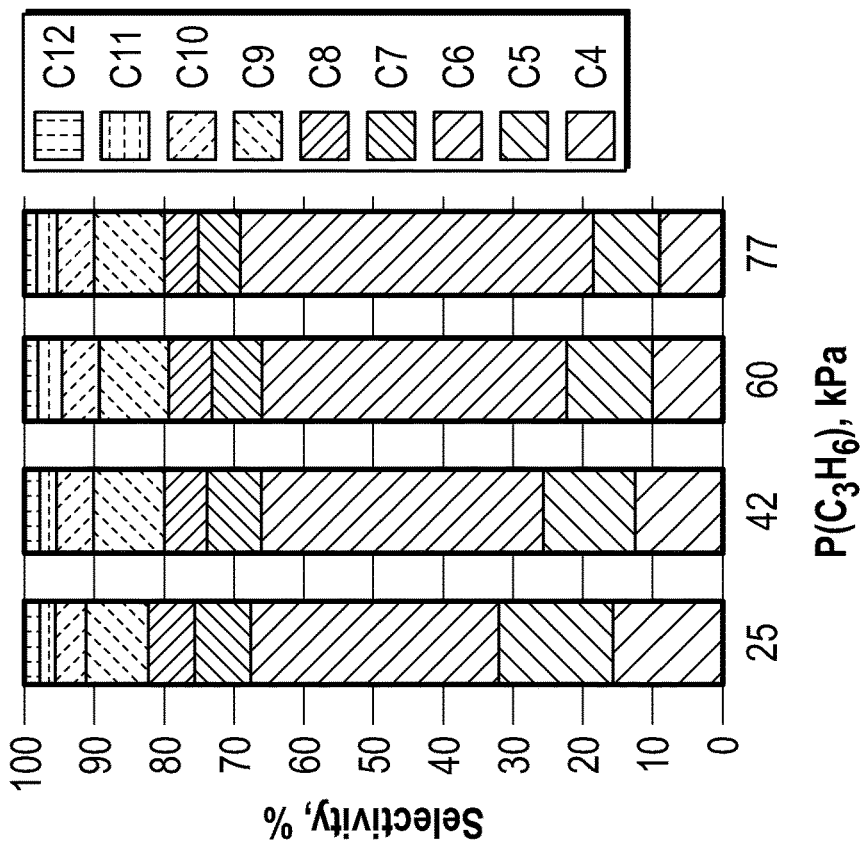
FIG. 5 is a bar graph of product distribution of propene oligomerization on a B-A-MFI-0.46 catalyst at 251° C., 1 atm total pressure with propene partial pressures of 25 to 77 kPa.
Figure 6:
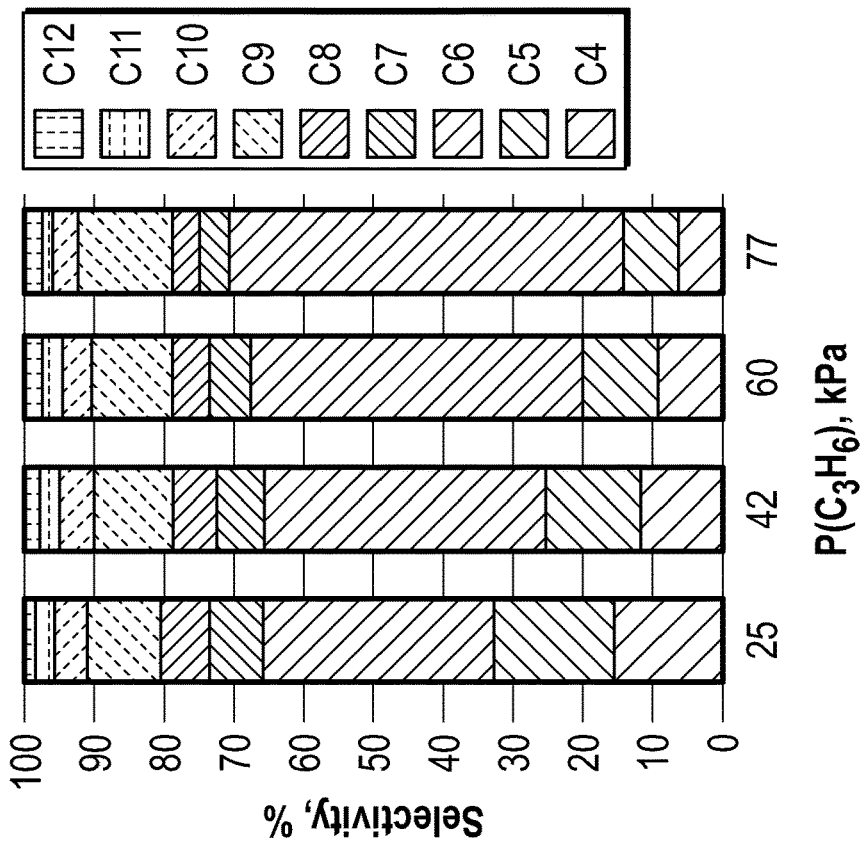
FIG. 6 is a bar graph of product distribution of propene oligomerization on a B-A-MFI-0.28 catalyst at 251° C., 1 atm total pressure with propene partial pressures of 25 to 77 kPa.
Figure 7:
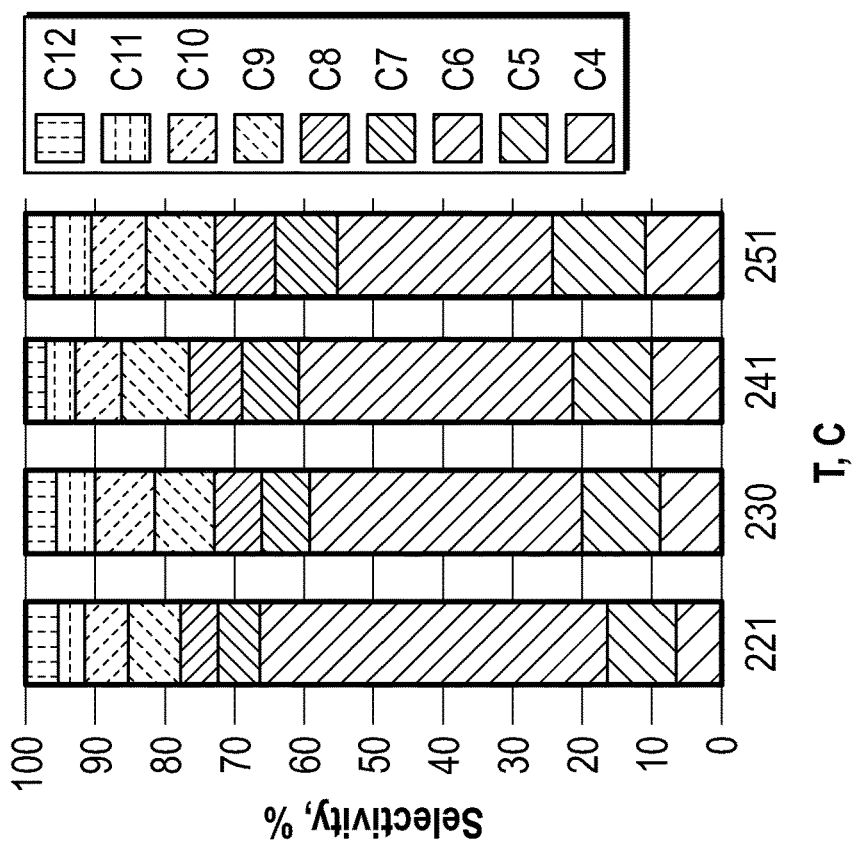
FIG. 7 is a bar graph of product distribution of propene oligomerization on a B—Al-MFI-0.23 catalyst at 251° C., 1 atm total pressure with propene partial pressures of 25 to 77 kPa.
Figure 8:
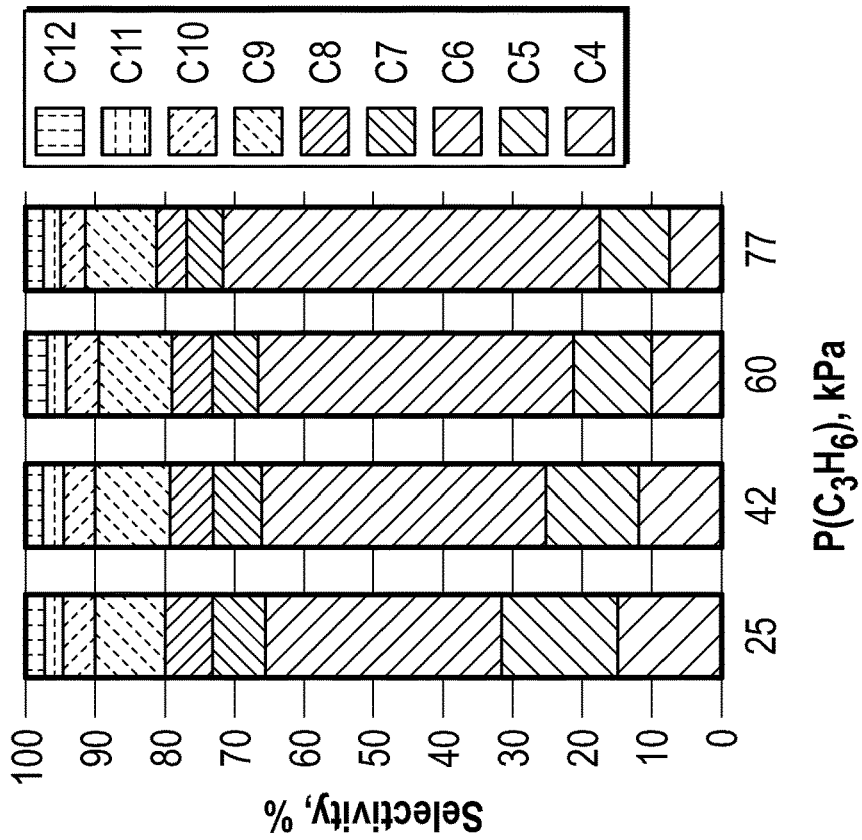
FIG. 8 is a bar graph of product distribution of propene oligomerization on commercial Al-MFI-0.32 catalyst at 75 kPa propene, 1 atm total pressure with temperatures of 221-251° C.
Figure 9:
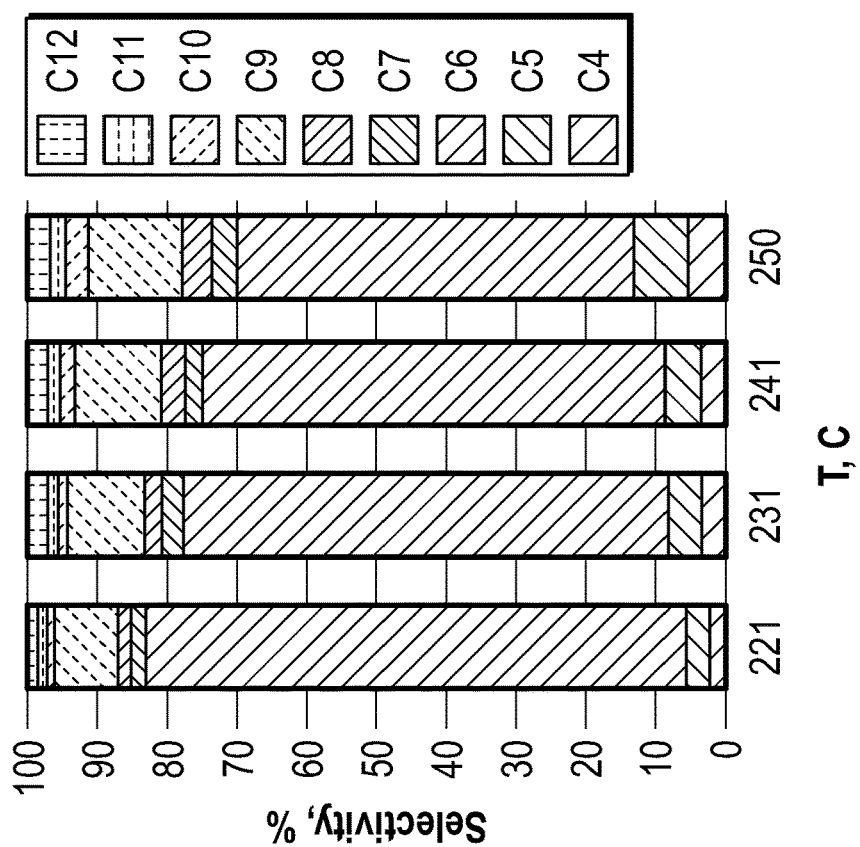
FIG. 9 is a bar graph of product distribution of propene oligomerization on B-A-MFI-0.56 catalyst at 75 kPa propene, 1 atm total pressure with temperatures of 221-251° C.
Figure 10:
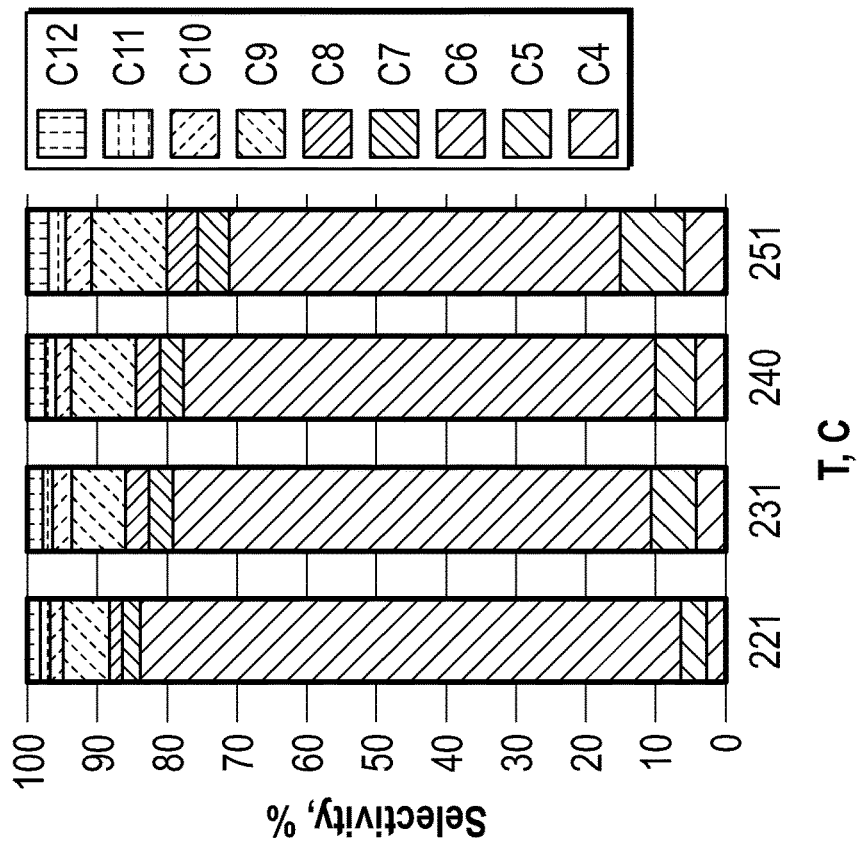
FIG. 10 is a bar graph of product distribution of propene oligomerization on B—Al-MFI-0.46 catalyst at 75 kPa propene, 1 atm total pressure with temperatures of 221-251° C.
Figure 11:
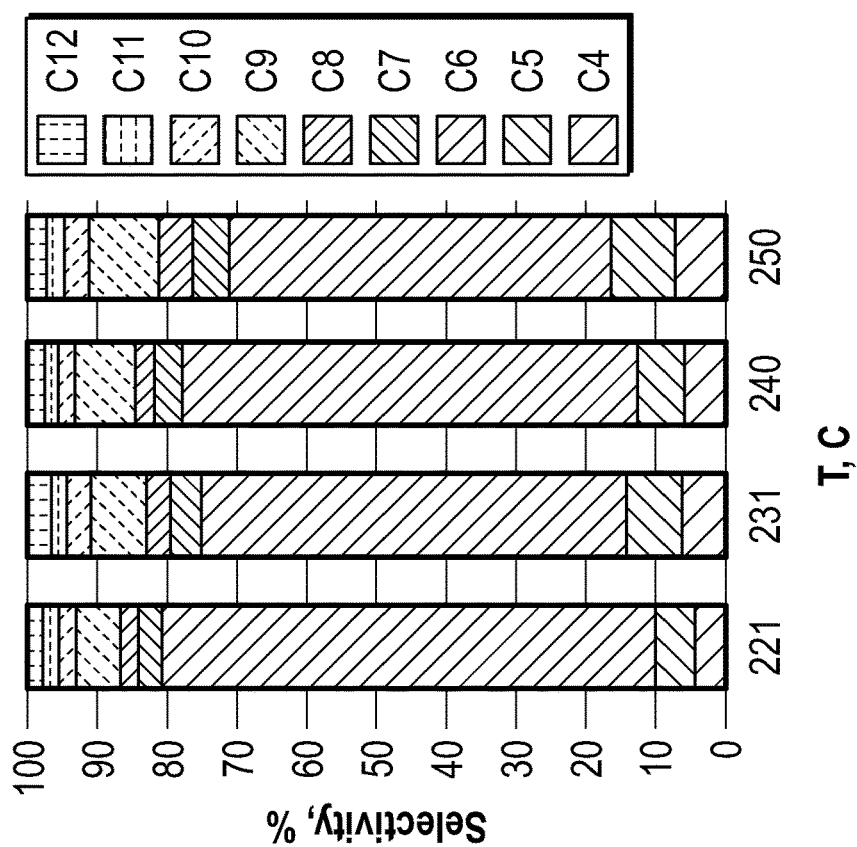
FIG. 11 is a bar graph of product distribution of propene oligomerization on B-A-MFI-0.28 catalyst at 75 kPa propene, 1 atm total pressure with temperatures of 221-251° C.
Figure 12:
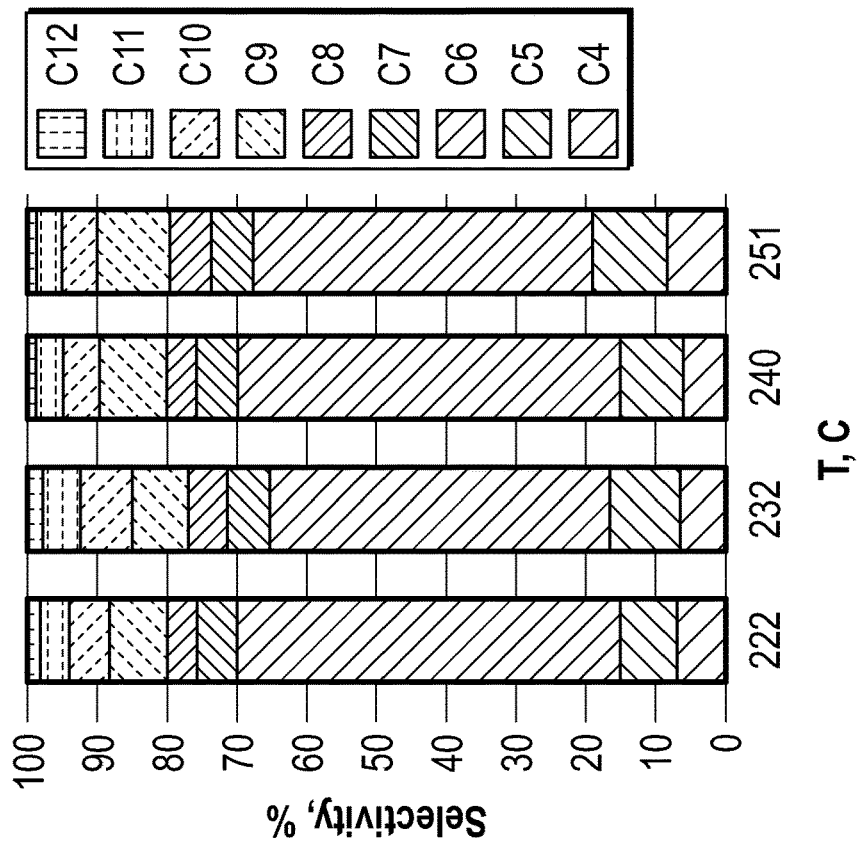
FIG. 12 is a bar graph of product distribution of propene oligomerization on B-A-MFI-0.23 catalyst at 75 kPa propene, 1 atm total pressure with temperatures of 221-251° C.

Kinetic measurements were carried out in a quartz plug-flow reactor with ⅜ or ½ inch O.D. containing 0.02-0.04 g of catalyst in a 10:1 dilution with $SiO_2$ to avoid hot spot formation. A thermocouple well with ⅛-inch O.D. and a thermocouple were placed through the catalyst bed at the bottom center to measure the reaction temperature. The reaction mixture contained 5% methane as an internal standard, 25%-77% propene, and the balance being argon. Products were analyzed by gas chromatography (Agilent 7890A) using DB-1 capillary column with flame ionization detector (FID). Between the reactor and the GC inlet, the gas line was maintained at 150° C. by heating tape to avoid condensation of products. Propene partial pressures were varied between 25-77 kPa and temperatures ranged from 221-251° C. All selectivities are reported at conversions below 5% at steady-state conditions Results and Discussion Measured Si/Al ratios and crystal sizes for commercially available Al-MFI zeolites and synthesized B-A-MFI zeolites are given in Table 1. SEM images of B—Al-MFI are shown in FIG. 2. Under the specific conditions of excess boron relative to aluminum (B/Al=7-70), crystal sizes and shapes are independent of aluminum content and depend primarily on the quantity of boron in the synthesis solution. These results agree with previous work by Cichocki and co-workers [Cichocki, A, et al. *Zeolites*. 10 (1990) 577-582], where crystal sizes of borosilicate MFI decrease with additional boron in the synthesis solution. However, any Brønsted acid sites that compensate framework boron atoms are unreactive compared to those that compensate framework aluminum atoms, as their deprotonation energies (an intrinsic measure of acid strength) are ~70 kJ mol$^{-1}$ higher, indicating that these are significantly weaker acid sites. Therefore, the observed oligomerization reactivity is due only to Brønsted acid sites at framework aluminum atoms.

TABLE 1

Catalyst properties of commercial and synthesized MFI

| Sample | Gel Si/Al | Gel Si/B | Al wt % | Crystal size, μm |
|---|---|---|---|---|
| Al-MFI-0.32[a] | 140 | N.A. | 0.32 | 0.8 |
| B—Al-MFI-0.56[b] | 75 | 13 | 0.56 | 11.0 |
| B—Al-MFI-0.46[b] | 75 | 2.6 | 0.46 | 0.4 |
| B—Al-MFI-0.28[b] | 150 | 13 | 0.28 | 8.7 |
| B—Al-MFI-0.23[b] | 150 | 2.6 | 0.23 | 0.3 |

[a]Obtained from Zeolyst International
[b]Synthesized at Purdue

Selectivities of propene oligomerization, measured under identical reaction conditions, are shown for the commercial Al-MFI zeolite and four B—Al-MFI zeolites synthesized at Purdue in FIGS. 3-7. The notation $C_n$ (n=4, 5, 6, 7, 8, 9, 10, 11, 12) indicates the olefin products containing n carbon atoms. Product selectivities at 251° C. and 75 kPa propene are given in Table 2. All B—Al-MFI zeolites show higher selectivity to primary oligomerization products ($C_6$, $C_9$, $C_{12}$) than secondary cracking products ($C_4$, $C_5$, $C_7$, $C_8$, $C_{10}$, $C_{11}$) compared to the commercial Al-MFI zeolites. For example, at 251° C. and 75 kPa propene, B—Al-MFI-0.56 shows 57.3% $C_6$ selectivity, while commercial Al-MFI-0.32 only shows 34.3% $C_6$ selectivity with no significant difference in selectivities to the other oligomerization products, $C_9$ and $C_{12}$. Higher oligomer selectivities were observed for all four B—Al-MFI catalysts with different Si/Al ratios and crystal sizes when compared to commercial A-MFI zeolites, indicating that boron addition during zeolite synthesis formed catalysts with different selectivity in these ranges (Si/Al=75-150, crystal size=0.3-11 μm) under the conditions used here. Higher propene partial pressure has been shown in the literature to increase oligomerization selectivity, which is also observed in the present study with both commercial and synthesized MFI zeolites.

TABLE 2

Selectivity comparison at 251° C. under 75 kPa C₃H₆

| Sample | Oligomerization product selectivity, % | | | Cracking product selectivity, % | | | | | |
|---|---|---|---|---|---|---|---|---|---|
| | $C_6$ | $C_9$ | $C_{12}$ | $C_4$ | $C_5$ | $C_7$ | $C_8$ | $C_{10}$ | $C_{11}$ |
| Al-MFI-0.32 | 34.3 | 10.0 | 3.6 | 10.5 | 13.2 | 8.8 | 8.0 | 6.9 | 4.6 |
| B—Al-MFI-0.56 | 57.3 | 10.4 | 2.9 | 6.5 | 8.2 | 4.7 | 4.3 | 3.5 | 2.3 |
| B—Al-MFI-0.46 | 56.1 | 13.5 | 3.3 | 6.2 | 7.6 | 4.1 | 4.0 | 3.0 | 2.2 |
| B—Al-MFI-0.28 | 50.1 | 10.0 | 1.9 | 8.5 | 10.4 | 6.0 | 5.4 | 4.7 | 2.9 |
| B—Al-MFI-0.23 | 54.5 | 10.1 | 2.7 | 7.9 | 9.3 | 5.1 | 4.7 | 3.6 | 2.2 |

The effect of temperature on selectivity was studied from 221-251° C. The results are shown in FIGS. 8-12 and in Table 3. Previous literature suggests that lower temperatures favor oligomerization over secondary cracking, which was observed in the present work with all MFI zeolites. All B—Al-MFI zeolites show higher $C_6$ selectivity with decreasing temperature between 221-251° C. compared to commercial Al-MFI zeolites. For example, at 221° C. and 75 kPa propene, B—Al-MFI-0.46 shows 77.0% $C_6$ selectivity, while commercial Al-MFI-0.32 only shows 50.0% $C_6$ selectivity. The increase in selectivity to $C_6$ products is most pronounced at the lowest temperature studied, which is commercially attractive as costs can be reduced by operating at lower reaction temperatures.

TABLE 3

Selectivity comparison at 221° C. under 75 kPa C₃H₆

| Sample | Oligomerization product selectivity, % | | | Cracking product selectivity, % | | | | | |
|---|---|---|---|---|---|---|---|---|---|
| | $C_6$ | $C_9$ | $C_{12}$ | $C_4$ | $C_5$ | $C_7$ | $C_8$ | $C_{10}$ | $C_{11}$ |
| Al-MFI-0.32 | 50.0 | 7.6 | 4.4 | 6.8 | 9.5 | 6.4 | 5.3 | 5.9 | 4.0 |
| B—Al-MFI-0.56 | 76.6 | 6.6 | 1.9 | 3.3 | 4.1 | 2.5 | 1.8 | 2.1 | 1.0 |
| B—Al-MFI-0.46 | 77.0 | 9.0 | 1.7 | 2.7 | 3.4 | 2.1 | 1.9 | 1.5 | 0.6 |
| B—Al-MFI-0.28 | 54.3 | 8.0 | 1.9 | 7.0 | 8.5 | 5.8 | 4.2 | 5.6 | 4.6 |
| B—Al-MFI-0.23 | 70.8 | 6.1 | 2.7 | 4.6 | 5.4 | 3.5 | 2.4 | 2.6 | 1.9 |

The above results show that the selectivity of olefin oligomerization can be improved via incorporation of boron into aluminosilicate frameworks, by reducing crystallite sizes without generating Brønsted acid sites that have been traditionally used for this chemistry.

An embodiment of the present disclosure is an oligomerization catalyst composition comprising: a crystalline, microporous zeolite with MFI topology; aluminum heteroatoms within the MFI structure having a first bulk aluminum content and first crystal size; and trivalent boron atoms within the support matrix substituted for tetravalent silicon atoms; wherein selectivity toward oligomers is enhanced compared to commercially available catalysts that only contain aluminum heteroatoms with similar bulk aluminum contents and crystal size.

An embodiment of the present disclosure is an oligomerization catalyst composition comprising: a crystalline, microporous zeolite with MFI topology; gallium heteroatoms within the MFI structure having a first bulk gallium content and first crystal size; and trivalent boron atoms within the support matrix substituted for tetravalent silicon atoms; wherein selectivity toward oligomers is enhanced compared to catalysts that only contain gallium heteroatoms with similar bulk gallium contents and crystal size.

An embodiment of the present disclosure is an oligomerization catalyst composition comprising: a crystalline, microporous zeolite with MFI topology; iron heteroatoms within the MFI structure having a first bulk iron content and first crystal size; and trivalent boron atoms within the support matrix substituted for tetravalent silicon atoms; wherein selectivity toward oligomers is enhanced compared to catalysts that only contain iron heteroatoms with similar bulk iron contents and crystal size.

The support can be a zeolite, such as ZSM-5 or a zeolite selected from a group that includes the following zeolite structures having framework type codes: TON; FER, MOR; OFF; MTW; MFI; ATN; AFO; AEL; AHT; EUO; MTT; MEL; ERI; and MFS. This catalyst composition can enhance selectivity toward oligomers of propene. In an embodiment the boron is present in an amount ranging from 0.01 wt to 5 wt % on an elemental basis of the catalyst composition. In an embodiment the aluminum is present in an amount from 0.01 to 5 wt % on an elemental basis of the catalyst composition. In an embodiment the gallium is present in an amount from 0.01 to 5 wt % on an elemental basis of the catalyst composition. In an embodiment the iron is present in an amount from 0.01 to 5 wt % on an elemental basis of the catalyst composition. In an embodiment the substitution of trivalent boron atoms for tetravalent silicon atoms do not behave as Brønsted acid sites for catalysis. In an embodiment the Brønsted acid sites that compensate framework boron atoms are unreactive compared to those that compensate framework aluminum or gallium or iron atoms. In an embodiment the Brønsted acid sites that compensate framework boron atoms are significantly weaker acid sites compared to those that compensate framework aluminum or gallium or iron atoms.

In an embodiment the B-A-MFI zeolite catalysts show higher selectivity to primary oligomerization products (C6, C9, C12) of propene than secondary cracking products (C4, C5, C7, C8, C10, C11), as compared to Al-MFI zeolite catalysts. In an embodiment the B—Ga-MFI zeolite catalysts show higher selectivity to primary oligomerization products (C6, C9, C12) of propene than secondary cracking products (C4, C5, C7, C8, C0, C11), as compared to Ga-MFI zeolite catalysts. In an embodiment the B—Fe-MFI zeolite catalysts show higher selectivity to primary oligomerization products (C6, C9, C12) of propene than secondary cracking products (C4, C5, C7, C8, C10, C11), as compared to Fe-MFI zeolite catalysts.

In an embodiment the boron addition formed catalysts with different selectivity to primary oligomerization products in the range of Si/Al greater than 75 as compared to comparable catalysts without boron. In an embodiment the boron addition formed catalysts with different selectivity to primary oligomerization products in these ranges of crystal size from 0.3 to 11 μm, as compared to comparable catalysts without boron. In an embodiment the crystal sizes of catalyst comprising borosilicate MFI decrease with additional boron content.

In an embodiment under the specific conditions of boron relative to aluminum (B/Al=0.1-5), crystal sizes and shapes are independent of aluminum content and depend primarily on the quantity of boron in the synthesis solution. In an embodiment under the specific conditions of boron relative to gallium (B/Ga=0.1-5), crystal sizes and shapes are independent of gallium content and depend primarily on the quantity of boron in the synthesis solution. In an embodiment under the specific conditions of boron relative to iron (B/Fe=0.1-5), crystal sizes and shapes are independent of iron content and depend primarily on the quantity of boron in the synthesis solution.

In an embodiment the catalyst is prepared using a hydrothermal synthesis protocol. In an embodiment the catalyst is prepared using a hydrothermal synthesis protocol combining, boron and aluminum heteroatoms with colloidal silica. In an embodiment the catalyst is prepared using a hydrothermal synthesis protocol combining boron and aluminum heteroatoms with colloidal silica, recovering solids via centrifugation followed by drying and calcination. In an embodiment the catalyst is prepared using a hydrothermal synthesis protocol combining, boron and gallium heteroatoms with colloidal silica. In an embodiment the catalyst is prepared using a hydrothermal synthesis protocol combining boron and gallium heteroatoms with colloidal silica, recovering solids via centrifugation followed by drying and calcination. In an embodiment the catalyst is prepared using a hydrothermal synthesis protocol combining, boron and iron heteroatoms with colloidal silica. In an embodiment the catalyst is prepared using a hydrothermal synthesis protocol combining boron and iron heteroatoms with colloidal silica, recovering solids via centrifugation followed by drying and calcination.

In an embodiment the catalyst was converted into their NH4-form by ion-exchange followed by calcination to convert to their H-form.

An embodiment of the present disclosure is a process for the oligomerization of alkenes to higher molecular weight hydrocarbons comprising: providing a catalyst comprising a support matrix having aluminum, or gallium, or iron heteroatoms within the support matrix and trivalent boron atoms within the support matrix substituted for tetravalent silicon atoms, wherein selectivity toward oligomers is enhanced by the boron content compared to commercially available catalysts that only contain aluminum or gallium, or iron heteroatoms with similar bulk contents and crystal size; contacting the catalyst with a feedstream comprising alkenes under oligomerization conditions; and oligomerization reactions occur converting a portion of the alkenes to higher molecular weight hydrocarbons. In an embodiment the higher molecular weight hydrocarbons are substantially free of aromatic hydrocarbons. In an embodiment the support is a zeolite. The support can be a zeolite, such as ZSM-5 or a zeolite selected from a group that includes the following zeolite structures having framework type codes: TON; FER, MOR; OFF; MTW; MFI; ATN; AFO; AEL; AHT; EUO; MTT; MEL; ERI; and MFS. This catalyst composition can make selectivity toward oligomers of propene enhanced. In an embodiment the boron is present in an amount ranging from 0.01 wt % to 5 wt % on an elemental basis of the catalyst composition. In an embodiment the aluminum is present in an amount from 0.01 to 5 wt % on an elemental basis of the catalyst composition. In an embodiment the gallium is present in an amount from 0.01 to 5 wt % on an elemental basis of the catalyst composition. In an embodiment the iron is present in an amount from 0.01 to 5 wt % on an elemental basis of the catalyst composition. In an embodiment the substitution of trivalent boron atoms for tetravalent silicon atoms do not behave as Brønsted acid sites for catalysis. In an embodiment the Brønsted acid sites that compensate framework boron atoms are unreactive compared to those that compensate framework aluminum, gallium or iron atoms. In an embodiment the Brønsted acid sites that compensate framework boron atoms are significantly weaker acid sites compared to those that compensate framework aluminum atoms. In an embodiment the B-A-MFI zeolite catalysts show higher selectivity to primary oligomerization products (C6, C9, C12) of propene than secondary cracking products (C4, C5, C7, C8, C10, C11), as compared to commercial Al-MFI zeolite catalysts. In an embodiment the boron addition formed catalysts with different selectivity to primary oligomerization products in the range of Si/Al greater than 75 as compared to comparable catalysts without boron. In an embodiment the boron addition formed catalysts with different selectivity to primary oligomerization products in these ranges of crystal size from 0.3 to 11 µm, as compared to comparable catalysts without boron. In an embodiment the crystal sizes of catalyst comprising borosilicate MFI decrease with additional boron content. In an embodiment under the specific conditions of boron relative to aluminum (B/Al=0.1-5), crystal sizes and shapes are independent of aluminum content and depend primarily on the quantity of boron in the synthesis solution. In an embodiment under the specific conditions of boron relative to gallium (B/Ga=0.1-5), crystal sizes and shapes are independent of gallium content and depend primarily on the quantity of boron in the synthesis solution. In an embodiment the catalyst is prepared using a hydrothermal synthesis protocol. In an embodiment the catalyst is prepared using a hydrothermal synthesis protocol combining, boron and aluminum heteroatoms with colloidal silica. In an embodiment the catalyst is prepared using a hydrothermal synthesis protocol combining boron and aluminum, gallium, iron, or combinations thereof, heteroatoms with colloidal silica, recovering solids via centrifugation followed by drying and calcination. In an embodiment the catalyst can be converted into their NH4-form by ion-exchange followed by calcination to convert to their H-form. In an embodiment the alkenes comprise $C_2$ to $C_{5+}$ alkenes. In an embodiment the process further comprises regeneration of the catalyst when needed. In an embodiment the feedstream comprises propene and selectivity to primary oligomerization products (C6, C9, C12) of propene is at least 80%. In an embodiment the feedstream comprises propene and conversion of propene to primary oligomerization products (C6, C9, C12) of propene is at least 5%. In an embodiment the feedstream comprises propene, the conversion of propene to primary oligomerization products (C6, C9, C12) of propene is at least 5% with selectivity primary oligomerization products (C6, C9, C12) of propene is at least 80%. In an embodiment these propene conversion and selectivity continues for at least 30 minutes, optionally at least 1 hour, optionally at least 2 hours, optionally at least 5 hours, optionally at least 10 hours, optionally at least 24 hours, optionally at least 48 hours, optionally at least 7 days, optionally at least 14 days, optionally at least 30 days. In an embodiment the feedstream comprises ethene and selectivity to primary oligomerization products (C4, C6, C9) of ethene is at least 80%. In an embodiment the feedstream comprises ethene and conversion to primary oligomerization products (C4, C6, C9) of ethene is at least 5%. In an embodiment the feedstream comprises ethene and conversion to primary oligomerization products (C4, C6, C9) of ethene is at least 5% and selectivity to primary oligomerization products (C4, C6, C9) of ethene is at least 80%. In an embodiment these ethene conversion and selectivity continues for at least 30 minutes, optionally at least 1 hour, optionally at least 2 hours, optionally at least 5 hours, optionally at least 10 hours, optionally at least 24 hours, optionally at least 48 hours, optionally at least 7 days, optionally at least 14 days, optionally at least 30 days.

An embodiment of the present disclosure is a method of making an oligomerization catalyst comprising: providing a support material; combining boron with aluminum, gallium, iron, or combinations thereof, heteroatoms with the support material; recovering solids via centrifugation; drying the recovered solids; and calcining the dried solids to form an oligomerization catalyst. In an embodiment the support material is colloidal silica. In an embodiment the support is selected from the group consisting of silicon dioxide, aluminum oxide, titanium dioxide, zeolites, silica-alumina, cerium dioxide, zirconium dioxide, magnesium oxide, metal modified silica, silica-pillared clays, silica-pillared micas, metal oxide modified silica-pillared mica, silica-pillared tetrasilicic mica, silica-pillared taeniolite, zeolite, molecular sieve, and combinations thereof. In an embodiment the support is a zeolite. The support can be a zeolite, such as ZSM-5 or a zeolite selected from a group that includes zeolite structures having framework type codes: TON; FER; MOR; OFF; MTW; MFI; ATN; AFO; AEL; AHT; EUO; MTT; MEL; ERI; and MFS. This catalyst composition can enhance selectivity toward oligomers of propene. In an embodiment the boron is present in an amount ranging from 0.01 wt % to 5 wt % on an elemental basis of the catalyst composition. In an embodiment the aluminum is present in an amount from 0.01 to 5 wt % on an elemental basis of the catalyst composition. In an embodiment the gallium is present in an amount from 0.01 to 5 wt % on an elemental basis of the catalyst composition. In an embodiment the iron is present in an amount from 0.01 to 5 wt % on an elemental basis of the catalyst composition. In an embodiment the combination of aluminum, gallium and iron is present in an amount from 0.01 to 5 wt % on an elemental basis of the catalyst composition. In an embodiment the substitution of trivalent boron atoms for tetravalent silicon atoms do not behave as Brønsted acid sites for catalysis. In an embodiment the Brønsted acid sites that compensate framework boron atoms are unreactive compared to those that compensate framework aluminum, gallium or iron atoms. In an embodiment the Brønsted acid sites that compensate framework boron atoms are significantly weaker acid sites compared to those that compensate framework aluminum atoms. In an embodiment the B-A-MFI, or B—Ga-MFI, or B—Fe-MFI zeolite catalysts show higher selectivity to primary oligomerization products (C6, C9, C12) of propene than secondary cracking products (C4, C5, C7, C8, C10, C11), as compared to commercial Al-MFI, Ga-MFI, or Fe-MFI zeolite catalysts. In an embodiment the boron addition formed catalysts with different selectivity to primary oligomerization products in the range of Si/Al greater than 75 as compared to comparable catalysts without boron. In an embodiment the boron addition formed catalysts with different selectivity to primary oligomerization products in these ranges of crystal size from 0.3 to 11 μm, as compared to comparable catalysts without boron. In an embodiment the crystal sizes of catalyst comprising borosilicate MFI decrease with additional boron content. In an embodiment under the specific conditions of boron relative to aluminum (B/Al=0.1-5), crystal sizes and shapes are independent of aluminum content and depend primarily on the quantity of boron in the synthesis solution. In an embodiment under the specific conditions of boron relative to gallium (B/Ga=0.1-5), crystal sizes and shapes are independent of gallium content and depend primarily on the quantity of boron in the synthesis solution. In an embodiment under the specific conditions of boron relative to iron (B/Fe=0.1-5), crystal sizes and shapes are independent of iron content and depend primarily on the quantity of boron in the synthesis solution. In an embodiment the catalyst is prepared using a hydrothermal synthesis protocol. In an embodiment the catalyst is prepared using a hydrothermal synthesis protocol combining, boron and aluminum heteroatoms with colloidal silica. In an embodiment the catalyst is prepared using a hydrothermal synthesis protocol combining boron and aluminum heteroatoms with colloidal silica, recovering solids via centrifugation followed by drying and calcination. In an embodiment the catalyst was converted into their NH4-form by ion-exchange followed by calcination to convert to their H-form.

The text above describes one or more specific embodiments of a broader disclosure. The disclosure also can be carried out in a variety of alternate embodiments and thus is not limited to those described here. The foregoing description of an embodiment of the disclosure has been presented for the purposes of illustration and description. It is not intended to be exhaustive or to limit the disclosure to the precise form disclosed. Many modifications and variations are possible in light of the above teaching. It is intended that the scope of the disclosure be limited not by this detailed description, but rather by the claims appended hereto.

What is claimed is:

1. A process for converting C2 to C5 alkenes to higher molecular weight hydrocarbons comprising:
   providing a catalyst comprising a support matrix having heteroatoms within the support matrix and trivalent boron atoms within the support matrix substituted for tetravalent silicon atoms, wherein the heteroatoms are chosen from the group consisting of aluminum, gallium, iron, and combinations thereof, wherein selectivity toward oligomers is enhanced by the presence of the boron compared to commercially available catalysts that only contain said heteroatoms with similar bulk heteroatom content and crystal size, and wherein the boron is present in an amount ranging from 0.01 wt % to 5 wt % on an elemental basis of the catalyst and the heteroatom is present in an amount from 0.01 wt % to 5 wt % on an elemental basis of the catalyst;
   contacting the catalyst with a feedstream comprising C2 to C5 alkenes within a reaction chamber; and
   converting at least a portion of the C2 to C5 alkenes within the reaction chamber at conditions sufficient to provide a higher molecular weight product comprising primary oligomerization products comprising C6, C9, C12 alkenes and secondary cracked products comprising C4, C5 and C7 alkenes.

2. The process according to claim 1 wherein the support matrix is a zeolite.

3. The process according to claim 2 wherein the zeolite is ZSM-5.

4. The process according to claim 2 wherein the zeolite comprises structures having framework type codes selected from the group consisting of: TON; FER, MOR, OFF; MTW; MFI; ATN; AFO; AEL; AHT; EUO; MTT; MEL; ERI; and MFS.

5. The process according to claim 1 wherein the C2 to C5 alkenes consist essentially of propylene or ethylene.

6. The process according to claim 1 further comprising regeneration of the catalyst when needed.

7. The process according to claim 1 wherein the support matrix is selected from the group consisting of silicon dioxide, aluminum oxide, titanium dioxide, zeolites, silica-alumina, cerium dioxide, zirconium dioxide, magnesium oxide, metal modified silica, silica-pillared clays, silica-pillared micas, metal oxide modified silica-pillared mica, silica-pillared tetrasilicic mica, silica-pillared taeniolite, zeolite, molecular sieve, and combinations thereof.

8. A process for converting C2 to C5 alkenes to higher molecular weight hydrocarbons, comprising;
   providing a support matrix;
   combining boron and one or more heteroatoms with the support matrix, the heteroatoms chosen from the group consisting of aluminum, gallium, iron, and combinations thereof;
   recovering solids via centrifugation;
   drying the recovered solids;
   calcining the dried solids to form an oligomerization catalyst, wherein the oligomerization catalyst comprises 0.01 wt % to 5 wt % of the boron on an elemental basis of the catalyst and 0.01 wt % to 5 wt % of the heteroatom on an elemental basis of the catalyst;
   contacting the catalyst with a feedstream comprising C2 to C5 alkenes within a reaction chamber; and
   converting at least a portion of the C2 to C5 alkenes within the reaction chamber at conditions sufficient to provide a higher molecular weight product comprising primary oligomerization products comprising C6, C9, C12 alkenes and secondary cracked products comprising C4, C5 and C7 alkenes.

9. The process according to claim 8 wherein the support matrix is colloidal silica.

10. The process according to claim 8 wherein the support matrix is selected from the group consisting of silicon dioxide, aluminum oxide, titanium dioxide, zeolites, silica-alumina, cerium dioxide, zirconium dioxide, magnesium oxide, metal modified silica, silica-pillared clays, silica-pillared micas, metal oxide modified silica-pillared mica, silica-pillared tetrasilicic mica, silica-pillared taeniolite, zeolite, molecular sieve, and combinations thereof.

11. The process according to claim 8 wherein the support matrix is a zeolite structure having framework type codes selected from the group consisting of: TON, FER, MOR; OFF; MTW, MFI, ATN; AFO; AEL; AHT; EUO, MTT; MEL; ERI; and MFS.

12. The process according to claim 8 wherein the crystalline structure has a crystal size of 0.3 microns to 11 microns.

13. The process according to claim 8 wherein the oligomerization conditions comprise a temperature of 100° C. to 500° C., and a pressure of 15 psig to 1500 psig.

14. The process according to claim 1 wherein the support matrix is synthesized using tetrapropyl ammonium (TPA) bromide and ethylenediamine (EDA).

15. The process according to claim 14 wherein the support matrix is synthesized using one part tetrapropyl ammonium (TPA) bromide to seven parts ethylenediamine (EDA).

16. The process according to claim 8 wherein the C2 to C5 alkenes consist essentially of propylene or ethylene.

* * * * *